United States Patent [19]

Endo et al.

[11] 4,378,990
[45] Apr. 5, 1983

[54] HERBICIDAL COMPOSITION

[75] Inventors: Keiji Endo, Shimada; Tomomi Toriyama; Kisaku Mori, both of Shizuoka, all of Japan

[73] Assignee: Schering Aktiengesellschaft, Berlin and Bergkamen, Fed. Rep. of Germany

[21] Appl. No.: 212,679

[22] Filed: Dec. 3, 1980

[30] Foreign Application Priority Data

Dec. 3, 1979 [JP] Japan .................................. 54-156561

[51] Int. Cl.³ ...................... A01N 43/02; A01N 31/00
[52] U.S. Cl. ......................................... 71/90; 71/108; 71/118; 71/124
[58] Field of Search ...................................... 71/90, 124

[56] References Cited

U.S. PATENT DOCUMENTS

| | | | |
|---|---|---|---|
| 4,039,588 | 8/1977 | Wilson et al. | 71/124 |
| 4,130,414 | 12/1978 | Arndt et al. | 71/90 |

FOREIGN PATENT DOCUMENTS

| | | | |
|---|---|---|---|
| 47-43815 | 11/1972 | Japan | 71/90 |
| 48-40931 | 6/1973 | Japan | 71/124 |
| 52-42853 | of 1977 | Japan | 71/90 |
| 50-55107 | 4/1980 | Japan | 71/124 |

*Primary Examiner*—Glennon H. Hollrah
*Attorney, Agent, or Firm*—Michael J. Striker

[57] ABSTRACT

Herbicidal composition containing 5-(N-phenylcarbamoylamino)-1,2,3-thiadiazole and either a diphenyl ether of the formula

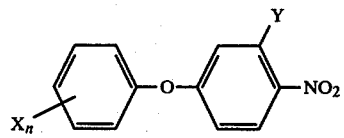

or an acetanilide of the formula

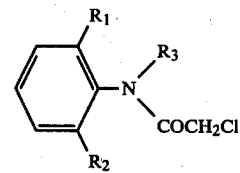

in which X is chlorine, methyl or trifluoromethyl, Y is hydrogen, lower alkoxy, ethoxyethoxyethoxy or methoxycarbonyl, n is 1 to 3, $R_1$ and $R_2$ are lower alkyl and $R_3$ is lower alkoxy-lower alkyl. The active components display synergistic effectiveness as broad-spectrum herbicides for perennial as well as annual weeds in paddy fields. Suitable solid and liquid carrier materials for the composition include emulsifiers.

3 Claims, No Drawings

HERBICIDAL COMPOSITION

BACKGROUND OF THE INVENTION

This invention relates to herbicidal compositions. Of particular concern are herbicidal compositions containing two kinds of compounds as active ingredients which possess remarkable synergistic effects that cannot be expected by application of compositions containing only one or the other type of compound.

In recent years, many excellent herbicides have been developed and employed to provide easy and rational control of annual weeds in paddy fields. A problem has arisen due to perennial weeds, previously occurring only locally, but of late spreading extensively along with the annual weeds. Measures for combatting this are eagerly being sought. Several factors can be cited to account for the propagation of such perennials, such as changes in cultivation and seeding methods and inadequate control of the cultivations. The principal factor apparently is the continued employment, for many consecutive years, of narrow-spectrum herbicides effective against annuals but ineffective with perennials. Under the circumstances, a great need exists for the development of broad-spectrum herbicides capable of combatting perennials as effectively as annuals.

Japanese patent publication No. 42853/77 discloses a plant growth regulator containing 5-(N-phenylcarbamoylamino)-1,2,3-thiadiazole. This compound has the effect of inhibiting weeds. Tests on the herbicidal properties of this regulator reveal that it has the effect of controlling the growth of annual broad-leaved weeds, annual *cyperaceae* weeds, and perennial weeds such as *Scirpus erectus* when applied during the pre-germination period or in the early stage of germination of weeds in paddy fields, but that it displays inferior results with *Barnyardgrass* and *Monochria Vaginalis*, which are strong harmful weeds. Additional disadvantages include a narrow herbicidal spectrum and narrow period of application.

The use in combination of various herbicides has been attempted, but it is widely recognized that in almost all instances the effect is a mere sum of the results attainable by the respective herbicides used alone, or, alternatively, that the effects of the respective herbicides compensate each other.

SUMMARY OF THE INVENTION

The object of the present invention is to provide a novel herbicidal composition not displaying the aforesaid defects, i.e., possessing a broad herbicidal spectrum effective for the eradication of both annual and perennial weeds.

The present herbicidal composition is characterized by containing as active components 5-(N-phenylcarbomoylamino)-1,2,3-thiadiazole and a diphenyl ether of the formula

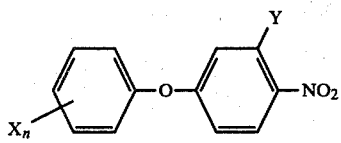
(I)

wherein the substituents X are the same or different and are chlorine, methyl or trifluoromethyl, Y is hydrogen, lower alkoxy, ethoxyethoxyethoxy, or methoxycarbonyl, and n is an integer from 1 to 3, or an acetanilide of the formula

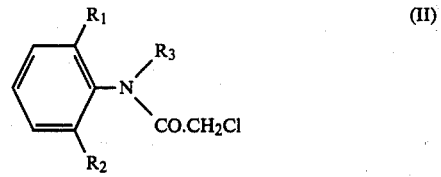
(II)

wherein $R_1$ is lower alkyl, $R_2$ is lower alkyl and $R_3$ is lower alkoxy-lower alkyl.

This composition exhibits remarkable synergism between the combined specific compounds, showing a broad herbicidal spectrum allowing for the eradication of both annual and perennial weeds. Employment of the novel herbicidal composition according to the present invention is usually before and after the transplantation of the rice into the paddy field. It is also applicable as herbicide in fields of such crops as cereals, pulses, and vegetables. Further suitable uses include fruit trees, lawns, forests, seedling fields and non-farming land.

The following non-limiting listing enumerates examples of compounds of formula (I) useful in herbicidal compositions according to the present invention:

| Compound Number | Compound Name |
|---|---|
| 1 | 2,4-dichlorophenyl-3'-methoxy-4'-nitrophenyl-ether |
| 2 | 2,4-dichlorophenyl-3'-ethoxyethoxyethoxy-4'-nitrophenyl ether |
| 3 | 2,4-dichlorophenyl-3'-methoxycarbonyl-4'-nitrophenylether |
| 4 | 2,4,6-trichlorophenyl-4'-nitrophenylether |
| 5 | 2-chloro-4-trifluoromethylphenyl-3'-ethoxy-4'-nitrophenylether |
| 6 | 3-methylphenyl-4'-nitrophenylether |
| 7 | 3,5-dimethylphenyl-4'-nitrophenylether |

The following non-limiting listing enumerates examples of compounds of formula II:

| | |
|---|---|
| 8 | 2',6'-diethyl-N—butoxymethyl-2-chloroacetanilide |
| 9 | 2',6'-diethyl-N—propoxyethyl-2-chloroacetanilide |
| 10 | 2',6'-dimethyl-N—isobutoxymethyl-2-chloroacetanilide |
| 11 | 2'-methyl-6'-tertiarybutyl-N—methoxymethyl-2-chloroacetanilide |

In the following, compounds 1 to 11 are the aforesaid compounds 1-11, and Compound A refers to the aforesaid 5-(N-phenyl-carbamoylamino)-1,2,3-thiadiazole.

The compounds of formulae I and II are all known compounds. They are known to exhibit excellent effects in the control of *gramineae* weeds, such as Barnyard grass, and of annual broad-leaved weeds, such as *Monochoria Vaginalis*, in each case when treated in the early period of their germination. However, these compounds have inferior effects with respect to perennial weeds such as *Cyperus serotinus, Sagittaria pygmaea,* and *Scirpus erectus*.

For purposes of application, the present herbicidal composition can be employed in any form of preparation. This would include such forms as granules, powder, wettable powder, emulsion and fine granules. Concerning the mixing ratio of the two components, it is suitable to admix 0.1 to 10 parts by weight of a compound of formula I or II, relative to one part by weight of compound A.

As carrier materials for the herbicidal compositions, solid carriers include talc, bentonite, clay, kaolin, diatomaceous earth, vermiculite, and calcium carbonate, among others. Effective liquid carriers include, e.g., benzene, alcohols, acetone, xylene, methyl naphthalene, dioxane, isophorone, and cyclohexanone, among others. Possible emulsifiers are, e.g., alkyl sulfuric acid esters, alkyl sulfonates, polyethylene glycol ethers and polyhydric alcohol esters, among others.

The novel features which are considered characteristic for the invention are set forth in particular in the appended claims. The invention itself, however, both as to its composition and its method of use, together with additional objects and advantages thereof, will be best understood from the following description of specific embodiments.

DESCRIPTION OF THE PREFERRED EMBODIMENTS

The following are examples of formulations for the present herbicidal compositions:

| Formulation 1: Wettable Powder | |
|---|---|
| Compound A | 10 parts |
| Compound 1 | 20 parts |
| diatomaceous earth | 65 parts |
| alkylbenzene sulfonic acid soda | 3 parts |
| formalin condensate of sodium naphthalene sulfonate | 2 parts |

These ingredients are thoroughly ground and mixed into a wettable powder.

| Formulation 2: Wettable Powder | |
|---|---|
| Compound A | 20 parts |
| Compound 8 | 15 parts |
| polyoxyethylene nonyl phenol ether | 2 parts |
| clay | 63 parts |

These ingredients are thoroughly ground and mixed into a wettable powder.

| Formulation 3: Emulsion | |
|---|---|
| Compound A | 10 parts |
| Compound 3 | 10 parts |
| polyethylene glycol ether surfactant | 10 parts |
| cyclohexanone | 30 parts |
| xylene | 40 parts |

These ingredients are mixed into an emulsion.

| Formulation 4: Granules | |
|---|---|
| Compound A | 4 parts |
| Compound 5 | 7 parts |
| ligninsulfonic acid soda | 6 parts |
| bentonite | 10 parts |
| clay | 73 parts |

These ingredients are mixed, ground and thoroughly kneaded, with water being added. Then, the resulting kneaded mixture is granulated and dried in granulated form.

| Formulation 5: Granules | |
|---|---|
| Compound A | 7 parts |
| Compound 9 | 7 parts |
| bentonite | 40 parts |
| diatomaceous earth | 46 parts |

These ingredients are mixed, ground and thoroughly kneaded, with the addition of water. Then, the resulting kneaded mixture is granulated and dried in granulated form.

Tests have been performed establishing the useful properties of the herbicidal compositions according to the present invention. These procedures are summarized in the following examples.

EXAMPLE 1

Test of herbicidal effect toward *Cyperus serotinus.*

Wagner pots measuring one five-thousandth ar in surface area were filled with paddy field soil (all vial loam) which was submerged 3 cm deep, and five tubers of *Cyperus serotinus* were transplanted into each pot. Three days later, granules prepared using individually either Compound A, Compound 1, or Compound 8, and also by using them in mixture with proportionate amounts of the respective compounds corresponding to the proportions indicated in Table 1 were applied to the submerged surfaces in such manner that the dosages of the respective compounds attained the proportions shown in Table 1. On the 30th day after the treatment, the residual *Cyperus serotinus* plants were pulled out and measured for their dry weight. Then, the residual mass percentage (%) of *Cyperus serotinus* was computed by the following equation:

$$\text{Residual mass percentage (\%)} = \frac{\text{dry weight of } Cyperus\ serotinus \text{ in treated zone}}{\text{dry weight of } Cyperus\ serotinus \text{ in control zone}} \times 100$$

The results are given in Table 1.

In order to clearly establish the synergistic effects of the present herbicidal compositions, the expected residual weed mass values were determined according to Colby's equation relating to synergistic effects:

$$\text{Expected residual weed mass value (\%) of mixed composition} = \frac{X(\%) \times Y(\%)}{100}$$

X(%) indicates the measured residual weed mass percentage (%) in case of independent use of the compound X, and Y(%) indicates the measured residual weed mass percentage (%) in case of independent use of the compound Y. These expected residual weed mass values are given in parentheses in Table 1.

Synergistic effects are established when the measured residual mass percentage (%) is less than the expected residual weed mass values (%).

EXAMPLE 2

Test of herbicidal effects on *Eleocharis acicularis*

The test was conducted under the same conditions as for Example 1, except that four roots of *Eleocharis acicularis*, instead of *Cyperus serotinus*, were transplanted into each pot. The results are shown in Table 2.

EXAMPLE 3

Test of herbicidal effects under field conditions

A test plot of 5 cm² was prepared as a paddy field and seeds or tubers of paddy field weeds such as *Echinochloa crusgalli, Monocharia vaginalis, Rotala indica, Callitriche stagnalis, Cyperus difformis, Scirpus erectus, Cyperus serotinus, Eleocharis acicularis*, and *Eleocharis plantaginea* were admixed with the soil during puddling. Subsequently, rice seedinglings in the four-leave stage were transplanted into the plot, and the soil was placed in 3 cm deep submerged condition. Four days after the rice transplantation, granules prepared by mixing miscellaneous compounds in the same manner as mentioned for Example 1 were applied to the water surface.

On the 40th day after the treatment, the residual weeds were pulled out and measured for dry weight, the values obtained being given in Table 3 as relative values opposed to control values.

The rank reading of the herbicidal effect and the damage is represented according to the following numerical scale:

| 0: | same as untreated control | |
|---|---|---|
| 1-2: | effects on the plant | slight |
| 3-4: | " | small |
| 5-6: | " | medium |
| 7-8: | " | large |
| 9-10: | " | extremely large |

EXAMPLE 4

Test of herbicidal effects

Soil from a paddy field (alluvial loam) was used to fill a Wagner pot measuring one five-thousandth of an ar in area, and, after water introduction and puddling, the soil was sown with seeds of *Echinochloa crusgalli, Monochroia vaginalis, Rotala indica, Callitriche stagnalis* and *Scirpus erectus*, and further planted with tubers of *Cyperus serotinus*, parent roots of *Eleocharis acicularis*, and rice seedlings in the three-leave stage. The soil was then placed under water, submerged 3 cm deep. On the third day after the rice transplantation, granules prepared by mixing miscellaneous compounds in the same manner as in Example 1 were applied to the submerged surface.

On the 30th day after treatment a survey was conducted in the same manner as in Example 3. The results are given in Table 4.

TABLE 1

| Test Compounds | | Compound 1 | | | | | Compound 8 | | | | |
|---|---|---|---|---|---|---|---|---|---|---|---|
| Dosage (g/10a) | | 80 | 40 | 20 | 10 | 0 | 80 | 40 | 20 | 10 | 0 |
| Compound A | 80 | 0 | 1 | 1 | 3 | 3 | 0 | 0 | 1 | 1 | 3 |
| | | (0.6) | (1.1) | (1.7) | (3) | | (1.0) | (1.8) | (2.4) | (3.0) | |
| | 40 | 1 | 2 | 3 | 6 | 13 | 1 | 2 | 3 | 5 | 13 |
| | | (2.) | (4.8) | (7.4) | (13.0) | | (4.4) | (7.9) | (10.4) | (13.0) | |
| | 20 | 2 | 3 | 3 | 5 | 27 | 1 | 4 | 6 | 8 | 27 |
| | | (5.4) | (10.0) | (15.4) | (27.0) | | (9.2) | (16.5) | (21.6) | (27.0) | |
| | 10 | 2 | 3 | 4 | 11 | 35 | 3 | 5 | 10 | 15 | 35 |
| | | (7.) | (13.0) | (20.0) | (35.0) | | (11.9) | (21.4) | (28.0) | (25.0) | |
| | 0 | 20 | 37 | 57 | 100 | 100 | 34 | 61 | 80 | 100 | 100 |

As is evident from Table 1, a noticeable synergism appears.

TABLE 2

| Test compounds | | Compound 1 | | | | | Compound 8 | | | | |
|---|---|---|---|---|---|---|---|---|---|---|---|
| Dosage (g/10a) | | 80 | 40 | 20 | 10 | 0 | 80 | 40 | 20 | 10 | 0 |
| Compoumd A | 80 | 0 | 1 | 2 | 3 | 7 | 0 | 0 | 1 | 1 | 7 |
| | | (0.7) | (1.7) | (4,3) | (3.5) | | (0.5) | (1.3) | (2.4) | (4.3) | |
| | 40 | 0 | 1 | 4 | 3 | 15 | 0 | 0 | 3 | 2 | 15 |
| | | (1.5) | (3.6) | (9.2) | (11.7) | | (1.1) | (2.9) | (5.1) | (9.2) | |
| | 20 | 2 | 3 | 6 | 11 | 26 | 0 | 1 | 3 | 8 | 26 |
| | | (2.6) | (6.2) | (15.9) | (20.3) | | (1.8) | (4.9) | (8.8) | (15.9) | |
| | 10 | 3 | 5 | 10 | 14 | 51 | 1 | 2 | 4 | 7 | 51 |
| | | (5.1) | (12.2) | (31.1) | (39.8) | | (3.6) | (9.7) | (17.3) | (31.1) | |
| | 0 | 10 | 24 | 61 | 78 | 100 | 7 | 19 | 34 | 61 | 100 |

As is evident from Table 2, a noticeable synergism appears.

TABLE 3

Herbicidal effects toward various weeds under field conditions

| Test Compounds/Dosage (g/10a) | | | | Annual Weeds | | | | Perennial Weeds | | | | harm to rice planted |
|---|---|---|---|---|---|---|---|---|---|---|---|---|
| | | | | Echinochloa crusgalli | Monochoria vaginalis | other broad leaved weeds | Cyperus difformis | Scirpus erectus | Cyperus serotinus | Eleocharis acicularis | Eleocharis plantaginea | |
| Com- | 25 | — | | 0 | 1 | 7 | 8 | 3 | 3 | 2 | 3 | 0 |
| pound | 50 | | | 1 | 3 | 9 | 10 | 4 | 6 | 2 | 6 | 0 |
| A | 100 | | | 3 | 6 | 10 | 10 | 5 | 6 | 4 | 7 | 0 |
| | 200 | | | 5 | 6 | 10 | 10 | 5 | 7 | 5 | 7 | 0 |
| Com- | 25 | Com- | 50 | 10 | 9 | 9 | 10 | 8 | 8 | 8 | 6 | 0 |
| pound | 50 | pound | 50 | 10 | 9 | 10 | 10 | 9 | 10 | 9 | 9 | 0 |
| A | 100 | 1 | 100 | 10 | 10 | 10 | 10 | 10 | 10 | 10 | 10 | 0 |
| — | | Com- | 50 | 9 | 6 | 9 | 10 | 1 | 1 | 0 | 0 | 0 |

TABLE 3-continued

Herbicidal effects toward various weeds under field conditions

| Test Compounds/Dosage (g/10a) | | | | Annual Weeds | | | | Perennial Weeds | | | | harm to rice planted |
|---|---|---|---|---|---|---|---|---|---|---|---|---|
| | | | | *Echinochloa crusgalli* | *Monochoria vaginalis* | other broad leaved weeds | *Cyperus difformis* | *Scirpus erectus* | *Cyperus serotinus* | *Eleocharis acicularis* | *Eleocharis plantaginea* | |
| | | pound 1 | 100 | 10 | 8 | 8 | 10 | 0 | 1 | 0 | 0 | 0 |
| | | 1 | 200 | 10 | 10 | 9 | 10 | 3 | 1 | 0 | 0 | 0 |
| Compound A | 50 | Compound 8 | 50 | 10 | 10 | 10 | 10 | 10 | 10 | 9 | 10 | 0 |
| | 100 | pound 8 | 100 | 10 | 10 | 10 | 10 | 10 | 10 | 10 | 10 | 0 |
| — | | Compound 8 | 50 | 9 | 7 | 9 | 10 | 4 | 1 | 2 | 0 | 0 |
| | | pound 8 | 100 | 10 | 9 | 9 | 10 | 6 | 2 | 3 | 0 | 0 |
| — | | — | | 0 | 0 | 0 | 0 | 0 | 0 | 0 | 0 | 0 |

TABLE 4

Test results concerning herbicidal effect

| Test Compoumds/Dosage (g/10a) | | | | *Echinochloa crusgalli* | annual broad leaved plants | *Scirpus erectus* | *Gyperus serotinus* | *Eleocharis aclcularis* | Harm to rice plan |
|---|---|---|---|---|---|---|---|---|---|
| Compound A | 5 | — | | 0 | 9 | 3 | 4 | 3 | 0 |
| | 10 | | | 3 | 9 | 4 | 5 | 5 | 0 |
| | 20 | | | 7 | 10 | 5 | 7 | 6 | 0 |
| — | | Compound 1 | 5 | 10 | 10 | 2 | 0 | 1 | 1 |
| | | | 10 | 10 | 10 | 3 | 0 | 2 | 1 |
| | | | 20 | 10 | 10 | 4 | 2 | 4 | 1 |
| Compound A | 5 | Compound 1 | 5 | 10 | 10 | 7 | 7 | 7 | 1 |
| | 5 | | 10 | 10 | 10 | 9 | 8 | 7 | 1 |
| | 10 | | 5 | 10 | 10 | 8 | 8 | 7 | 1 |
| | 10 | | 10 | 10 | 10 | 10 | 10 | 9 | 1 |
| — | | Compound 2 | 5 | 9 | 10 | 3 | 1 | 1 | 1 |
| | | | 10 | 9 | 10 | 4 | 1 | 3 | 1 |
| | | | 20 | 10 | 10 | 5 | 3 | 4 | 1 |
| Compound A | 5 | Compound 2 | 5 | 8 | 10 | 8 | 8 | 9 | 1 |
| | 5 | | 10 | 10 | 10 | 8 | 9 | 9 | 1 |
| | 10 | | 5 | 10 | 10 | 9 | 10 | 10 | 1 |
| | 10 | | 10 | 10 | 10 | 9 | 10 | 10 | 1 |
| — | | Compound 3 | 5 | 9 | 10 | 3 | 1 | 2 | 1 |
| | | | 10 | 10 | 10 | 5 | 3 | 3 | 1 |
| | | | 20 | 10 | 10 | 7 | 3 | 4 | 1 |
| Compound A | 5 | Compound 3 | 5 | 9 | 10 | 10 | 8 | 8 | 1 |
| | 5 | | 10 | 10 | 10 | 10 | 8 | 8 | 1 |
| | 10 | | 5 | 9 | 10 | 10 | 10 | 10 | 1 |
| | 10 | | 10 | 10 | 10 | 10 | 10 | 10 | 1 |
| — | | Compound 4 | 10 | 9 | 9 | 2 | 0 | 1 | 1 |
| | | | 20 | 10 | 10 | 3 | 1 | 1 | 1 |
| | | | 40 | 10 | 10 | 5 | 1 | 2 | 1 |
| Compound A | 5 | Compound 4 | 10 | 9 | 10 | 9 | 6 | 7 | 1 |
| | 5 | | 20 | 10 | 10 | 10 | 8 | 8 | 1 |
| | 10 | | 10 | 8 | 10 | 7 | 7 | 8 | 1 |
| | 10 | | 20 | 10 | 10 | 9 | 8 | 9 | 1 |
| | 20 | | 10 | 10 | 10 | 10 | 9 | 9 | 1 |
| | 20 | | 20 | 10 | 10 | 10 | 9 | 10 | 1 |
| — | | Compound 5 | 2.5 | 3 | 10 | 3 | 1 | 2 | 1 |
| | | | 5 | 10 | 10 | 5 | 1 | 3 | 2 |
| | | | 10 | 10 | 10 | 7 | 3 | 4 | 2 |
| Compound A | 2.5 | Compound 5 | 2.5 | 7 | 10 | 10 | 6 | 8 | 1 |
| | 5 | | 2.5 | 7 | 10 | 9 | 6 | 9 | 1 |
| | 5 | | 5 | 10 | 10 | 10 | 8 | 9 | 1 |
| | 5 | | 10 | 10 | 10 | 10 | 8 | 10 | 2 |
| | 10 | | 2.5 | 10 | 10 | 10 | 9 | 10 | 1 |
| | 10 | | 5 | 10 | 10 | 10 | 10 | 10 | 1 |
| | 10 | | 10 | 10 | 10 | 10 | 10 | 10 | 1 |
| — | | Compound 6 | 15 | 0 | 3 | 1 | 0 | 0 | 0 |
| | | | 30 | 0 | 7 | 3 | 0 | 0 | 0 |
| | | | 60 | 1 | 9 | 4 | 0 | 0 | 0 |
| Compound A | 10 | Compound 6 | 15 | 2 | 9 | 6 | 6 | 7 | 0 |
| | 10 | | 30 | 5 | 10 | 8 | 6 | 6 | 0 |
| | 20 | | 15 | 8 | 10 | 9 | 8 | 8 | 0 |
| | 20 | | 30 | 8 | 10 | 10 | 9 | 9 | 0 |
| — | | Compound 7 | 15 | 0 | 0 | 0 | 0 | 0 | 0 |
| | | | 30 | 0 | 2 | 0 | 0 | 1 | 0 |
| | | | 60 | 3 | 9 | 5 | 1 | 1 | 0 |
| Compound A | 10 | Compound 7 | 15 | 5 | 9 | 7 | 6 | 7 | 0 |
| | 10 | | 30 | 6 | 10 | 8 | 7 | 6 | 0 |
| | 20 | | 15 | 9 | 10 | 9 | 8 | 7 | 0 |
| | 20 | | 30 | 9 | 10 | 10 | 10 | 10 | 0 |
| — | | Compound 8 | 2.5 | 9 | 4 | 3 | 0 | 1 | 0 |
| | | | 5 | 10 | 7 | 5 | 1 | 1 | 0 |

TABLE 4-continued

Test results concerning herbicidal effect

| Test Compounds/Dosage (g/10a) | | | | Echinochloa crusgalli | annual broad leaved plants | Scirpus erectus | Gyperus serotinus | Eleocharis aclcularis | Harm to rice plan |
|---|---|---|---|---|---|---|---|---|---|
| | | | 10 | 10 | 7 | 7 | 2 | 2 | 0 |
| Compound A | 2.5 | Compound 8 | 2.5 | 9 | 9 | 9 | 6 | 8 | 0 |
| | 5 | | 2.5 | 10 | 10 | 7 | 6 | 9 | 0 |
| | 5 | | 5 | 9 | 10 | 10 | 8 | 6 | 0 |
| | 5 | | 10 | 10 | 10 | 9 | 8 | 9 | 0 |
| | 10 | | 2.5 | 10 | 10 | 8 | 8 | 7 | 0 |
| | 10 | | 5 | 10 | 10 | 9 | 9 | 9 | 0 |
| | 10 | | 10 | 10 | 10 | 10 | 10 | 10 | 0 |
| — | | Compound 9 | 2.5 | 9 | 4 | 3 | 1 | 2 | 0 |
| | | | 5 | 10 | 6 | 6 | 1 | 2 | 0 |
| | | | 10 | 10 | 7 | 7 | 3 | 3 | 0 |
| Compound A | 2.5 | Compound 9 | 2.5 | 9 | 9 | 9 | 6 | 8 | 0 |
| | 5 | | 2.5 | 9 | 10 | 8 | 7 | 8 | 0 |
| | 5 | | 5 | 10 | 10 | 9 | 8 | 9 | 0 |
| | 5 | | 10 | 10 | 10 | 10 | 9 | 9 | 0 |
| | 10 | | 2.5 | 10 | 10 | 9 | 9 | 7 | 0 |
| | 10 | | 5 | 10 | 10 | 10 | 10 | 10 | 0 |
| | 10 | | 10 | 10 | 10 | 10 | 10 | 10 | 0 |
| — | | Compound 10 | 2.5 | 9 | 7 | 2 | 0 | 1 | 0 |
| | | | 5 | 9 | 8 | 3 | 0 | 1 | 0 |
| | | | 10 | 9 | 9 | 5 | 2 | 2 | 0 |
| Compound A | 2.5 | Compound 10 | 2.5 | 9 | 9 | 10 | 6 | 7 | 0 |
| | 5 | | 2.5 | 10 | 10 | 9 | 6 | 6 | 0 |
| | 5 | | 5 | 9 | 10 | 9 | 7 | 6 | 0 |
| | 5 | | 10 | 10 | 10 | 10 | 7 | 7 | 0 |
| | 10 | | 2.5 | 10 | 10 | 9 | 8 | 6 | 0 |
| | 10 | | 5 | 10 | 10 | 10 | 9 | 9 | 0 |
| | 10 | | 10 | 10 | 10 | 10 | 10 | 10 | 0 |
| | | Compound 11 | 2.5 | 10 | 3 | 3 | 0 | 1 | 0 |
| | | | 5 | 10 | 2 | 5 | 2 | 3 | 0 |
| | | | 10 | 10 | 7 | 7 | 2 | 4 | 0 |
| Compound A | 2.5 | Compound 11 | 2.5 | 10 | 9 | 10 | 6 | 7 | 0 |
| | 5 | | 2.5 | 10 | 10 | 9 | 6 | 6 | 0 |
| | 5 | | 5 | 10 | 10 | 10 | 7 | 7 | 0 |
| | 5 | | 10 | 10 | 10 | 10 | 7 | 8 | 0 |
| | 10 | | 2.5 | 10 | 10 | 9 | 9 | 7 | 0 |
| | 10 | | 5 | 10 | 10 | 10 | 9 | 9 | 0 |
| | 10 | | 10 | 10 | 10 | 10 | 10 | 10 | 0 |
| — | — | | | 0 | 0 | 0 | 0 | 0 | 0 |

As explained and exemplified above, the combination of 5-(N-phenylcarbamoylamino)-1,2,3-thiadiazole with a compound of the aforesaid formula I or II results in considerable synergistic action with respect to perennial weeds such as Cyperus serotinus, Eleocharis acicularis, and Eleocharis plantaginea, that cannot be sufficiently controlled by the respective ingredients used alone. The combinations are additionally remarkably effective with annual weeds which can be sufficiently controlled by the respective ingredients used alone at their usual dosages.

Combined use of these compounds according to the present invention presents the advantages of increased herbicidal effectiveness, broadened herbicidal spectrum, extended period for residual effect, expanded suitable application period, and increased selectivity between crops and weeds, each of which aspects is recognized as being a matter of great agricultural importance.

It will be understood that each of the elements described above, or two or more together, may also find a useful application in other types of herbicidal compositions differing from the types described above.

While the invention has been illustrated and described as embodied in a herbicidal composition having as active components 5-(N-phenylcarbomoylamino)-1,2,3-thiadiazole and a diphenylether of formula I or an acetanilide of the formula II, it is not intended to be limited to the details described, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Herbicidal composition consisting essentially of as active components an effective amount of a mixture of 5-(N-phenylcarbamoylamino)-1,2,3-thiadiazole and a diphenyl ether of the formula

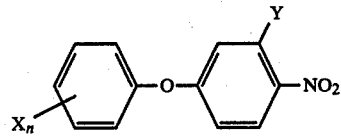

wherein the substituents X are chlorine, Y is hydrogen or lower alkoxy, and n is an integer from 1 to 3, in a ratio from about 8:1 to 1:8 parts by weight, and an inert carrier material.

2. Herbicidal composition according to claim 1, wherein said diphenyl ether is 2,4-dichlorophenyl-3'-methoxy-4'-nitrophenyl ether.

3. Herbicidal composition according to claim 1, wherein said diphenyl ether is 2,4,6-trichlorophenyl-4'-nitrophenylether.

* * * * *